United States Patent
Krogmann et al.

(10) Patent No.: US 6,246,239 B1
(45) Date of Patent: Jun. 12, 2001

(54) PATIENT BED FOR USE WITH MAGNETIC RESONANCE IMAGING APPARATUS

(75) Inventors: Henrik Krogmann, Erlangen; Rainer Kuth, Herzogenaurach; Gerald Lenz, Neunkirchen am Brand; Herbert Weiler, Alling; Hartmut Nagel, Rudolstadt-Pflanzwirbach, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/136,018

(22) Filed: Aug. 19, 1998

(30) Foreign Application Priority Data

Aug. 25, 1997 (DE) ................................ 197 36 884

(51) Int. Cl.⁷ .............................. G01V 3/00; G01R 33/20
(52) U.S. Cl. ............................................................ 324/318
(58) Field of Search ............................................. 324/318

(56) References Cited

U.S. PATENT DOCUMENTS

| 4,968,937 | * 11/1990 | Akgun | 324/318 |
|---|---|---|---|
| 5,027,818 | * 7/1991 | Bova et al. | 600/427 |
| 5,347,252 | 9/1994 | Ries | 324/318 |
| 5,615,430 | 4/1997 | Nambu et al. | 5/600 |
| 5,735,278 | * 4/1998 | Hoult et al. | 324/318 |

FOREIGN PATENT DOCUMENTS 92 18 322   1/1994 (DE) .

OTHER PUBLICATIONS

"Intraoperative Diagnostic and Interventional Magnetic Resonance Imaging in Neurosurgery," Tronnier et al, Neurosurgery, vol. 40, No. 5, May 1997, pp. 891–902.

\* cited by examiner

Primary Examiner—Jay Patidar
Assistant Examiner—Dixomara Vargas
(74) Attorney, Agent, or Firm—Schiff Hardin & Waite

(57) ABSTRACT

An expanded diagnostic NMR installation with operating functionality contains an NMR imaging apparatus with a patient bed for transporting a patient into an imaging volume of the NMR imaging apparatus. An operating column for receiving the patient bed is arranged next to the NMR imaging apparatus at a fixed distance therefrom along the longitudinal direction of motion of the patient bed. The operating column contains a swinging mechanism for rotating or pivoting the patient bed around a vertical axis.

4 Claims, 3 Drawing Sheets

PATIENT BED FOR USE WITH MAGNETIC RESONANCE IMAGING APPARATUS

BACKGROUND OF THE INVENTION

1. Field of the Invention

The invention relates to an expanded diagnostic NMR device with operating functionality with a conventional NMR device that includes a patient bed for transporting a patient into an imaging volume of the NMR device.

2. Description of the Prior Art

Among diagnostic NMR devices with operating functionality are open systems that have another, primarily lateral, access to the imaging volume in addition to the patient access. U.S. Pat. No. 5,347,252 discloses an open NMR device whose C-shaped magnet construction enables a lateral access perpendicular to the patient access. The NMR device permits operations on a patient in the center of the imaging volume with continuous monitoring by means of NMR imaging. With the aid of the NMR imaging, the access of an operating instrument can be tracked or a therapy can be monitored, for example.

The advantages of an intraoperative NMR imaging in the diagnosis and therapy in connection with neurosurgery are described in the article by Tronnier et al. entitled "Intraoperative Diagnostic and Interventional Magnetic Resonance Imaging in Neurosurgery", published in Neurosurgery, Vol. 40, No. 5, May 1997, pp. 891–902. A special patient transport system with an air cushion shuttle is utilized therein in order to transport the patient to the NMR device and back again to the place of surgery. The transport with air cushion shuttle proved to be a safer solution for a vibrationless transport compared to a shuttle with wheels, shock absorbers and springs. The patient transport system is indeed freely mobile; however, it requires great care in the coupling of the patient bed with the NMR device. Compressed air terminals are additionally required for operating the air cushions. Furthermore, the time required for the employing this patient transport is significant.

German Utility Model G 9218322.0 teaches a means for minimally invasive therapy and microtherapy with a computed tomography apparatus and an appertaining patient holding device designed to function as an operation and treatment space. The patient holding device is arranged in stationary fashion, while the housing of the computed tomography apparatus can be displaced in a linearly guided fashion by a drive and guides. To allow swinging the patient holding device functioning as an operating table into a position perpendicular to the path of motion of the housing of the computed tomography apparatus in an emergency, the patient holding device is mounted on a rotating vertical column.

U.S. Pat. No. 5,615,430 discloses a medical bed system for a number of medical devices such as a CT x-ray device and a radiation therapy device, for example. The bed system includes a single patient bearing for all devices, whereby a patient can be examined in the different devices without transfer. The patient bearing is mounted on a swivelling arm and a rotating table such that it can be moved to a desired location. Without giving further details, it is mentioned in this patent that other imaging devices such as NMR devices (MRI) or SPECT devices can be operated with the bed system as well.

SUMMARY OF THE INVENTION

It is an object of the present invention to provide an expanded diagnostic NMR device with which an operation of a patient with NMR imaging is possible, and which simultaneously has no significant limitations relative to currently typical operating tables with respect to the functionality.

The object is inventively achieved in an NMR installation having operating column for receiving the patient bed arranged next to an NMR imaging device at a fixed distance in a longitudinal direction of motion of the patient bed, the operating column containing a horizontal swing mechanism for swinging the patient bed around a vertical axis. It is thus possible to conduct a surgical intervention in the relatively low amplitude stray field of the NMR device, whereby there is only a limited need for NMR-compatible operating instruments. Since the patient is freely accessible outside the NMR device, known and proven surgical methods can be used for carrying out the intervention. Limitations, as exist in an intervention within the imaging volume of the NMR device due to the limited access possibilities, are not significant. At the same time, an intraoperative vibrationless displacement of the patient is possible for checking progress during the course the interventional procedure by means of NMR imaging. Furthermore, the full tomographical functionality of the NMR device is maintained by disposing the operating column at a distance from the NMR device.

DESCRIPTION OF THE PREFERRED EMBODIMENTS

Figure 1:
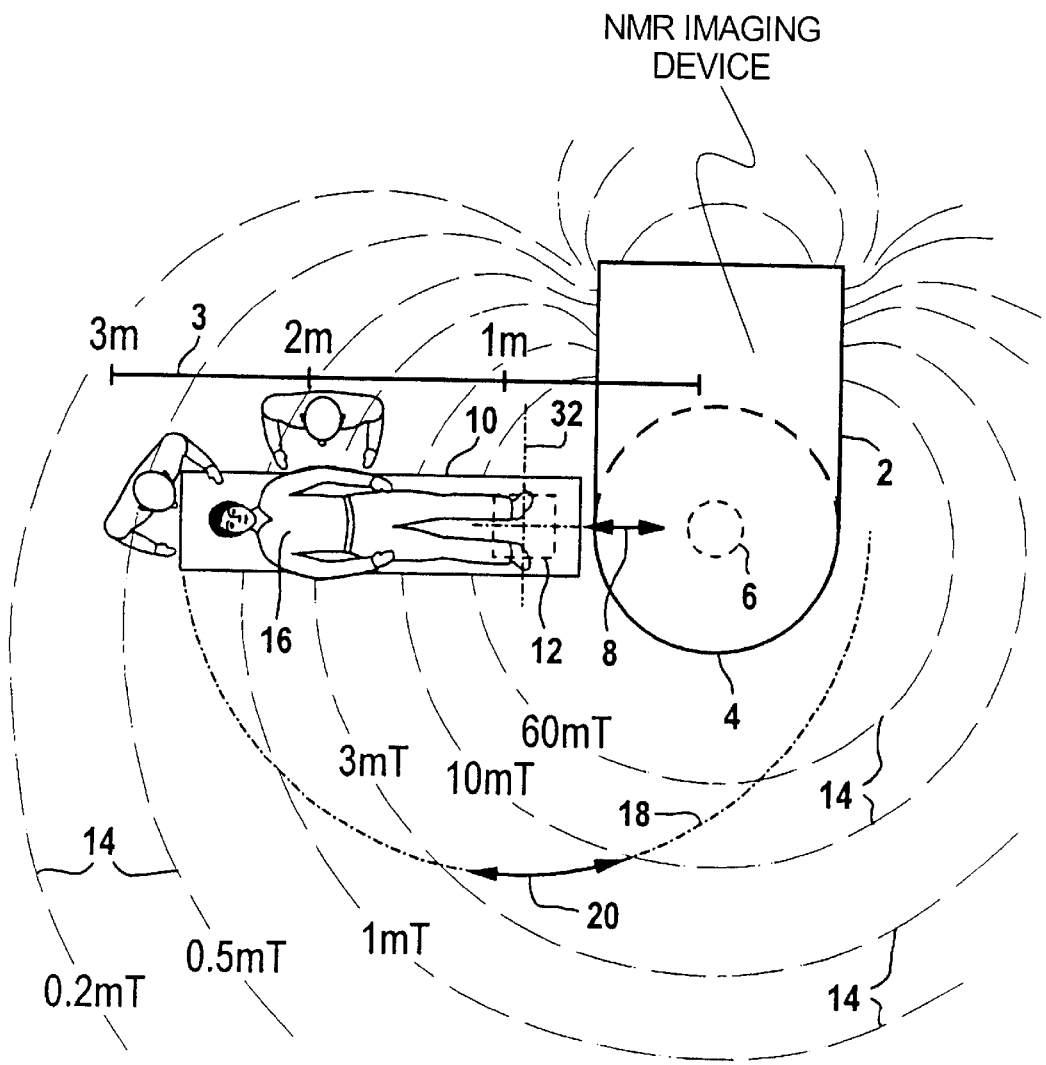
FIG. 1 is a schematic plan view of an expanded NMR device with a C-shaped magnet, constructed in accordance with the principles of the present invention

FIG. 1 schematically depicts a diagnostic NMR imaging device 2 with a Cshaped magnet structure. For purposes of illustration a longitudinal scale 3 is included in FIG. 1. The magnet structure of the NMR imaging device includes two pole shoes 4, spaced from each other, between which a substantially spherical imaging volume 6 is located. The basic structure of the magnet system is extensively described in U.S. Pat. No. 5,347,252 or in German OS 37 37 133. The diagnostic NMR device is produced and marketed by the firm Siemens AG under the name "Magnetom Open".

An operating column 12 is securely mounted at a distance of about 1 m from the NMR device 2 in a direction of motion (symbolized by a double arrow) of a patient bed 10. The operating column 12 is arranged in the stray field (dashed line 14) of the basic field magnet. The operating column 12 is located in a stray magnetic field of the order of magnitude of 60 mT. The stray field is low enough to be able to use conventional electromotors in the column 12 as displacement drives.

The operating column 12 can contain components composed of ferromagnetic materials; the magnet of the magnetic resonance device 2 is accordingly first shimmed following the assembly of the operating column 12; i.e. the magnetic field in the imaging volume 6 is homogenized by suitable small magnets in the form of electromagnets or permanent magnets, or by additional ferromagnetic iron elements as well. Disturbances which may arise due to the ferromagnetic portions of the operating column 12 are thus compensated.

With the aid of a Lafette, also called a shuttle, the patient bed 10 is driven into the operating room from an operating prep room, for example, and is interlocked with the operating column 12. Once it is positioned with respect to height via the operating column 12, the patient bed 10 can then be driven by the operating column 12 in the direction of motion 8 into the NMR device 2. It can also be swung between the pole shoes 4 by a swinging mechanism, symbolized by a dashed semicircle 18 with curved double arrow 20. In the NMR device the region of interest (ROI) of the patient can then be positioned in the imaging volume corresponding to the direction of motion 8.

Figure 2:
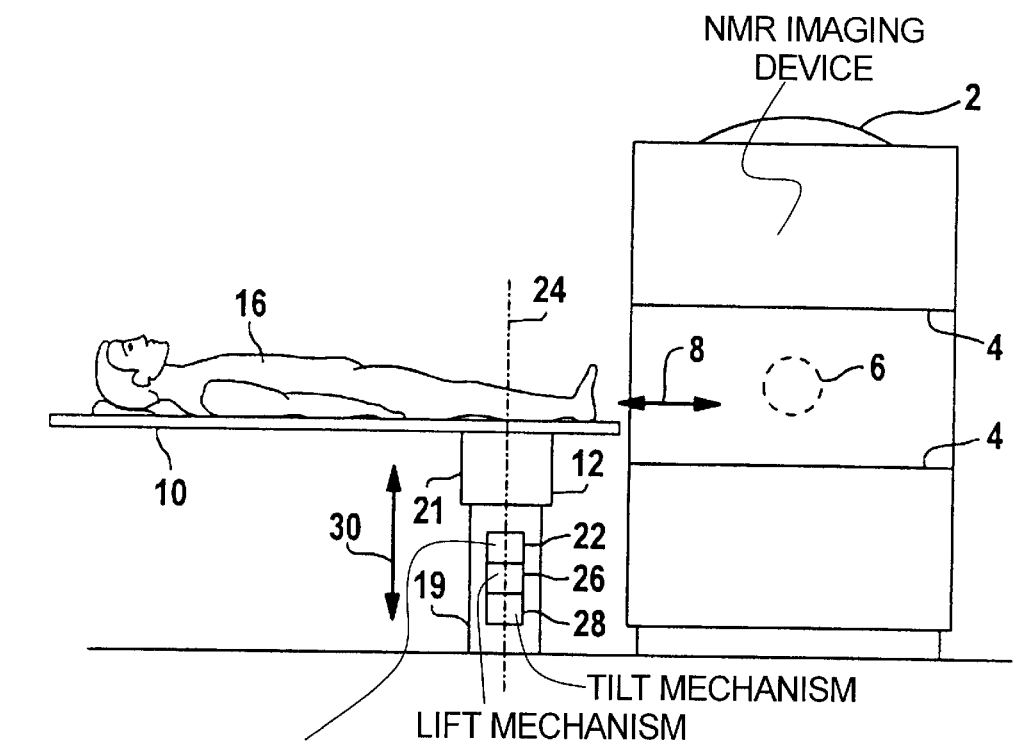
FIG. 2 is a side view of the NMR device according to FIG. 1, with the lift function depicted.

FIG. 2 shows a front view of the NMR device 2 with the operating column 12 on which the patient bed 10 is detachably secured. The operating column includes a securely mounted base part 19 to which another part 21 is flexibly mounted. The interlocking mechanism for the patient bed 10 is located at the upper side of the part 21. A swinging mechanism 22 with a motor operator (possibly with a gear train or belt for swinging around a horizontal axis 24), and a lift mechanism 26 containing an electric drive, e.g. in the form of a rotatable spindle, and a tilt mechanism 28 with an electromotor drive, are schematically drawn in the operating column 12. The lifting path symbolized by a double arrow 30—for the patient bed 10 extends from the bottom of the assembly to a height of e.g. 75 cm to 1.10 m.

Figure 3:
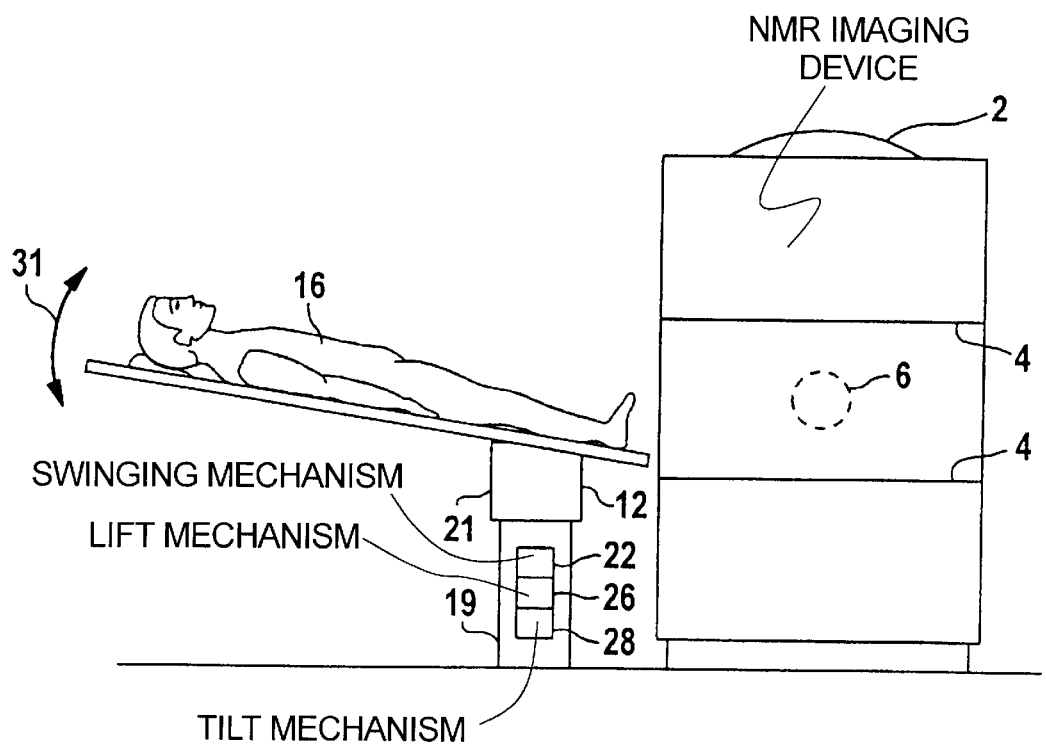
FIG. 3 is a side view of the NMR device according to FIG. 1, with the tilt function depicted.

FIG. 3 likewise shows the patient bed 10 in tilted position in a frontal view, whereby a tilt angle of up to (positive) 20° is possible for reducing blood pressure in the head during head operations. The tilting path is symbolized by a double arrow 31. The tilt axis lies horizontally and perpendicularly to the patient bed 10 and is characterized in FIG. 1 by reference numeral 32.

Figure 4:
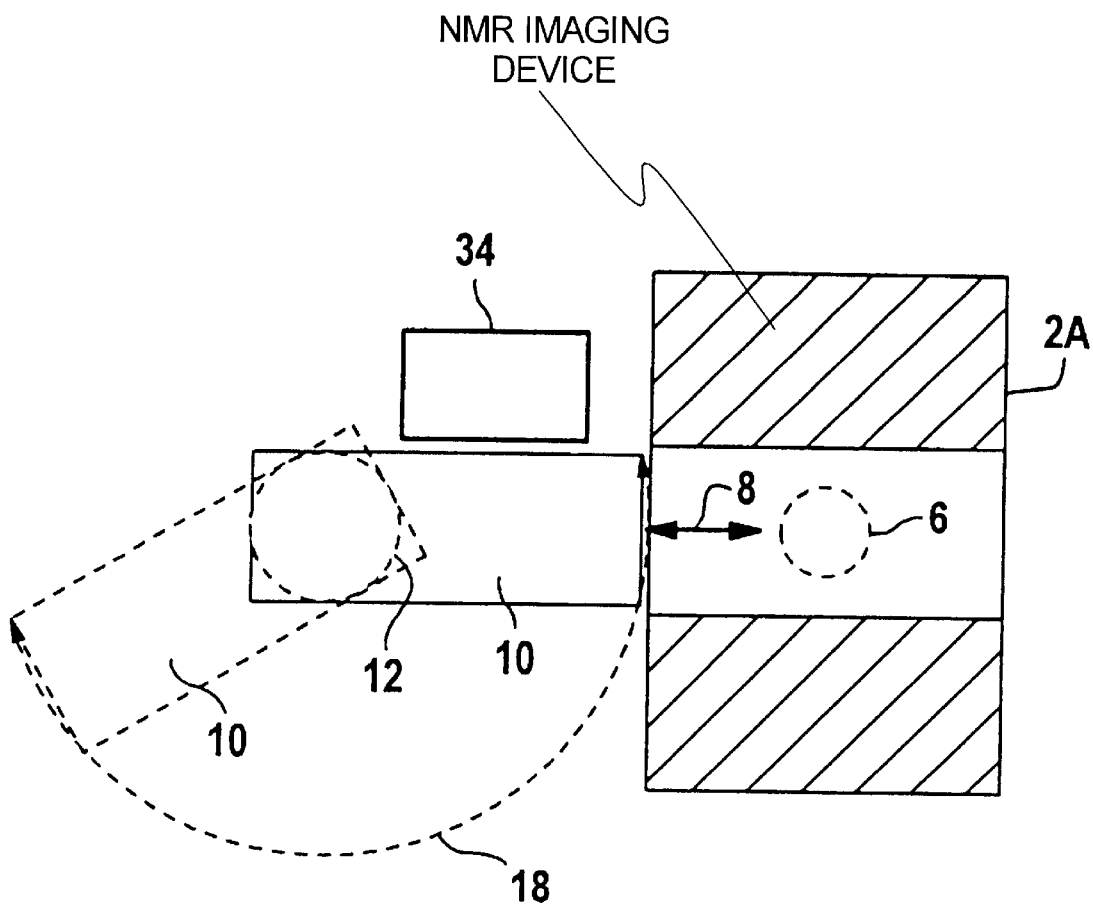
FIG. 4 is a schematic plan view of an expanded NMR device with a superconductive basic field magnet, constructed in accordance with the principles of the present invention.

FIG. 4 schematically shows a plan view of an expanded NMR device 2A with a superconducting tubular magnet. Besides the patient access no other lateral access to the imaging volume 6 is provided therein. Given utilization of an actively shielded magnet, the stray field in the exterior space falls off sharply so that an operating column 12 partially constructed of ferromagnetic materials can also be securely mounted therein at a distance from the NMR device 2A. The magnet is also shimmed therein after assembly of the operating column 12. The operating column 12 is likewise arranged at a distance in the direction of motion 8 such that the patient bed 10 with the patient 16 can be driven into the examination space to the imaging volume 6, while still allowing a free access outside the patient. By means of the swinging mechanism previously described the patient bed 10 with the patient 16 can then be swung into an operating position, depicted here in dashed fashion. The utilization of conventional, i.e. ferromagnetic, instruments is also possible therein. There is still space in a zone 34 between the operating column 12 and the NMR device 2A for anaesthesia devices and other monitoring devices in use during the operation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A diagnostic nuclear magnetic resonance installation comprising:

a magnetic resonance imaging apparatus having an imaging volume;

a patient bed movable along a longitudinal axis into and out of said imaging volume;

an operating column disposed at a fixed distance along said longitudinal axis from said magnetic resonance imaging apparatus, on which said patient bed is mounted; and a swinging mechanism contained in said operating column for swinging said patient bed around a vertical axis outside of the image volume.

2. A diagnostic nuclear magnetic resonance installation as claimed in claim 1 further comprising a lift mechanism contained in said column for raising and lowering said patient bed.

3. A diagnostic nuclear magnetic resonance installation as claimed in claim 1 further comprising a tilt mechanism contained in said operating column for tilting said patient bed around a horizontal axis.

4. A diagnostic nuclear magnetic resonance installation as claimed in claim 1 wherein said swinging mechanism contains a drive comprising an electric motor.

* * * * *